(12) United States Patent
Frazier et al.

(10) Patent No.: US 7,875,010 B2
(45) Date of Patent: Jan. 25, 2011

(54) INCONTINENCE DEVICE

(76) Inventors: LaToya Nicole Frazier, 7907 River Rock Way, Curtis Bay, MD (US) 21226; Anna Blakney Frazier, 7907 River Rock Way, Curtis Bay, MD (US) 21226

(*) Notice: Subject to any disclaimer, the term of this patent is extended or adjusted under 35 U.S.C. 154(b) by 339 days.

(21) Appl. No.: 12/133,348

(22) Filed: Jun. 4, 2008

(65) Prior Publication Data

US 2008/0300448 A1 Dec. 4, 2008

Related U.S. Application Data

(60) Provisional application No. 60/932,787, filed on Jun. 4, 2007.

(51) Int. Cl.
*A61F 5/44* (2006.01)
*A61M 1/00* (2006.01)

(52) U.S. Cl. .................. 604/329; 604/327; 604/347

(58) Field of Classification Search ............ 604/327, 604/329, 347
See application file for complete search history.

(56) References Cited

U.S. PATENT DOCUMENTS

| | | |
|---|---|---|
| 2,483,079 A | 9/1949 | Williams |
| 3,194,238 A | 7/1965 | Breece, Jr. |
| 3,601,125 A | 8/1971 | Moss |
| 4,846,817 A | 7/1989 | Mohr et al. |
| 4,866,508 A | 9/1989 | Eichelberger et al. |
| 4,904,248 A | 2/1990 | Vaillancourt |
| 5,004,463 A | 4/1991 | Nigay |
| 5,053,027 A | 10/1991 | Manfredi |
| 5,411,495 A | 5/1995 | Willingham |
| 5,735,835 A | 4/1998 | Holland |
| 6,151,721 A | 11/2000 | Whitfield |
| 6,342,049 B1 | 1/2002 | Nichols |
| 6,505,355 B1 | 1/2003 | Mutke |
| 7,077,833 B2 | 7/2006 | Bonham |
| 2002/0026161 A1 | 2/2002 | Grundke et al. |
| 2005/0033248 A1 | 2/2005 | Machida et al. |
| 2005/0075615 A1 | 4/2005 | Bonham |
| 2006/0069359 A1 | 3/2006 | DiPalma et al. |
| 2007/0005031 A1 | 1/2007 | Charles |

*Primary Examiner*—Jacqueline F. Stephens

(57) ABSTRACT

An incontinence device for wearing by a female is disclosed. A urine collection trough has an elongated open top end that is adapted to fit around the labia area of the female, encompassing her urethra. The trough has at least one non-rigid side wall and includes a drainage aperture in a lower portion thereof and a vaginal anchor means at an upper portion thereof. The vaginal anchor means is preferably a resilient protruding member fixed to the upper portion of the side wall of the trough. A drainage conduit is fixed at an upper end thereof to the drainage aperture that has at a lower end a valve means having an open position and a closed position. Preferably, the at least one side wall includes at least one attachment aperture therethrough, such that the device may be fixed to articles of clothing with straps, buttons, or the like.

13 Claims, 3 Drawing Sheets

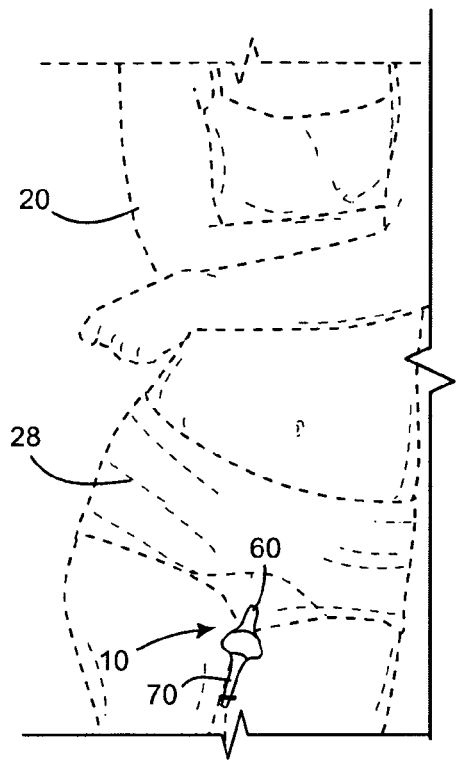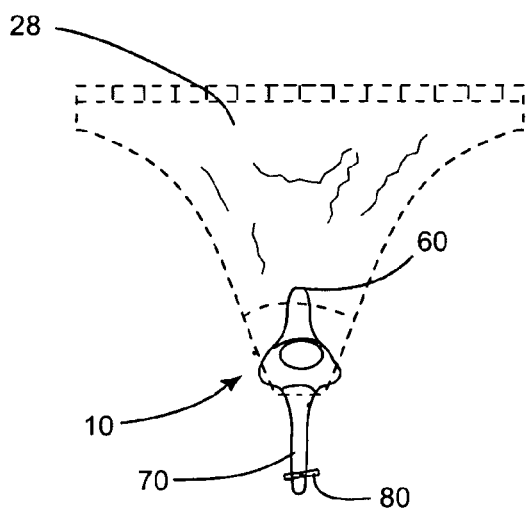
FIG. 1
FIG. 2
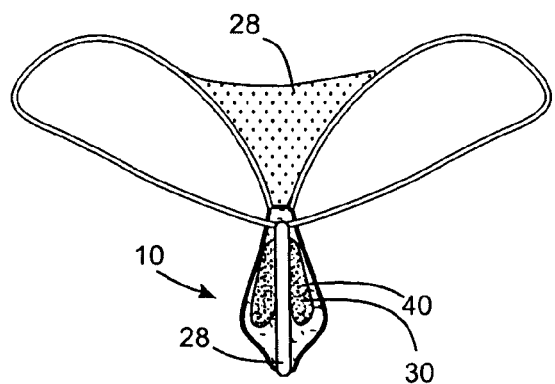
FIG. 3

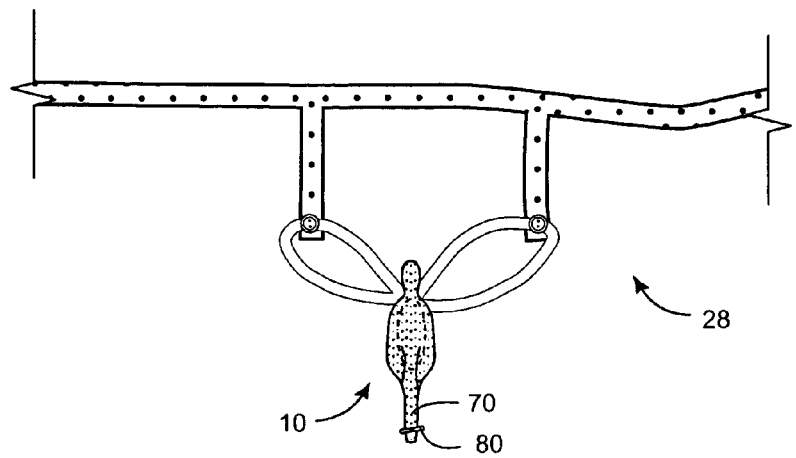
FIG. 7
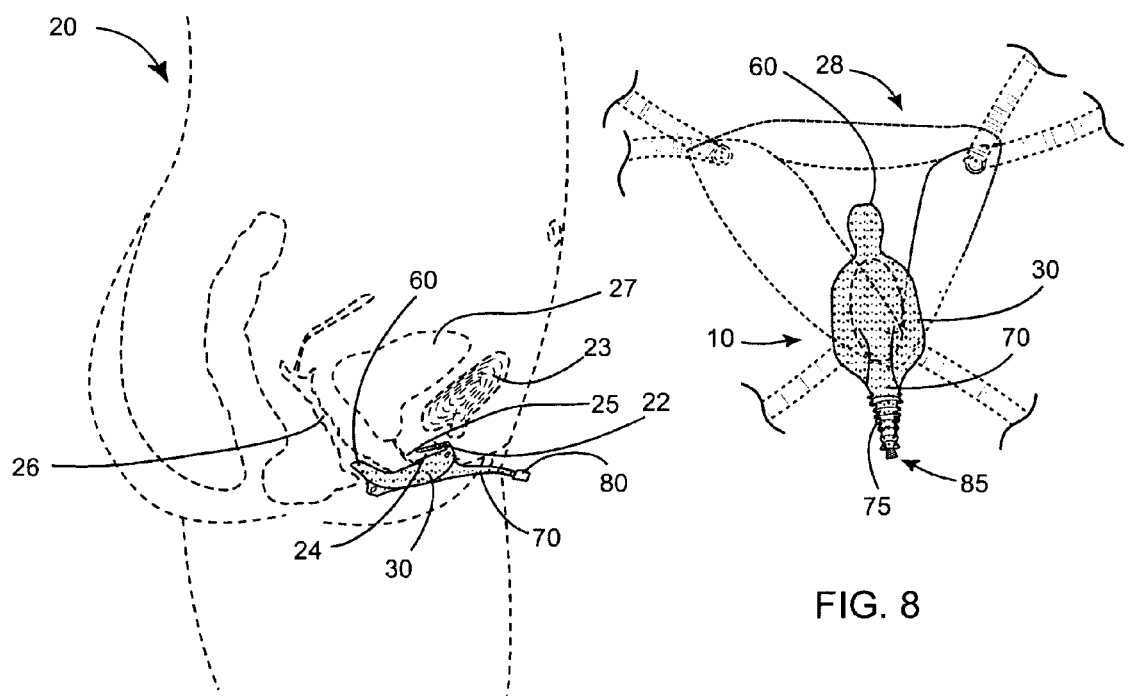
FIG. 6
FIG. 8

INCONTINENCE DEVICE

CROSS-REFERENCE TO RELATED APPLICATIONS

This application claims the benefit of U.S. Provisional Patent Application 60/932,787, filed on Jun. 4, 2007, and incorporated herein by reference.

STATEMENT REGARDING FEDERALLY SPONSORED RESEARCH AND DEVELOPMENT

Not Applicable.

FIELD OF THE INVENTION

This invention relates to incontinence devices, and more particularly to a vaginally insertable incontinence device.

DISCUSSION OF RELATED ART

Prior art incontinence devices for females typically include a cup-shaped receptacle for catching urine from the female and delivering it to a urine bag, or the like. Prior art device are typically held to the female with a variety of belts, straps, tight-fitting undergarments, adhesive strips, and the like, so as to be non-invasive. For example, the following prior art patents and patent applications teach such devices: U.S. Pat. Nos. 4,886,508 to Washington on Dec. 12, 1989; 4,904,248 to Vallancourt on Feb. 27, 1990; 5,053,027 to Manfredi on Oct. 1, 1991; 5,411,495 to Willingham on May 2, 1995; 5,735,835 to Holland on Apr. 7, 1998; 6,151,721 to Whitfield on Nov. 28, 2000; 6,505,355 to Mutke on Jan. 14, 2003; 2002/0026161 to Grundke et al. on Feb. 28, 2002; and 2006/0069359 to DiPalma et al. on Mar. 30, 2006.

Such prior art devices have the drawback that, even with the attachment means taught in each, relying on non-invasive means is at best sporadically reliable. Frequently such devices become misaligned, resulting in leakage and soiling of garments. Further, such devices are typically uncomfortable in that they are made from a material that is somewhat rigid and cannot be pressed substantially flat against the body between the user's garments.

Another prior art device, disclosed in U.S. Pat. No. 2,483,079 to Williams on Sep. 27, 1949, teaches a device that is inserted vaginally and additional held with a belt and strap arrangement. In such a device, the inserted portion also forms part of a conduit through which urine is conducted to a discharge tube. Such a device requires the use of a vaginally-inserted portion, and thus there is no alternate attachment means for women who do not desire such insertion.

Therefore, there is a need for an incontinence device that is able to lie substantially flat between the woman and one or more garments, yet still maintain a suitable seal around the woman's urethra, when the woman is in either a prone or an upright position. Such a needed invention would be comfortable to wear, and would allow the option of a removable vaginally-inserted anchoring means of various shapes, sizes, and orientations so as to allow for individual comfort preferences. The needed device would allow for use with a urine bag secured, for example, around the user's leg, or for discharge directly into a toilet, bed pan, or the like. Such a device would provide a drainage conduit that is flexible, and has a valve means to selectively open or close the drainage conduit at will. The needed invention would further provide for a variety of additional attachment means, including specific garments that would be made to more firmly, yet comfortably, hold the device in place, even when the user is physically active. Such a needed invention would further be made from a comfortable, medical-grade, safe, flexible material of any color or transparency that is easily washed or disposed of. The needed invention would further provide additional attachment means that the user can use as necessary or as preferred, and a drainage tube that is adjustable, flexible so that it can be oriented either forward or rearward, and retractable and collapsible. The present invention accomplishes these objectives.

SUMMARY OF THE INVENTION

The present device is an incontinence device for wearing by a female. A urine collection trough has an elongated open top end that is adapted to fit around the labia area of the female, encompassing her urethra. The trough has at least one non-rigid side wall, preferably being made from a resilient silicone rubber, latex, vinyl, or the like, and is made from a relatively thin opaque, transparent or translucent, of any color, such resilient material so that the device will lie substantially flat against the female when worn between the female and an article of clothing.

The trough further includes a drainage aperture in a lower portion thereof, and a vaginal anchor means at an upper portion thereof. The vaginal anchor means is preferably a resilient protruding member fixed to the upper portion of the side wall of the trough. Preferably the protruding member is removably fixed to the upper portion, such as by a mechanical fastening means such as mechanical snaps, tongue-in-groove, or the like. As such, the woman may decide whether or not to use the device with the vaginal anchor means, or may select an alternate vaginal anchor means based on comfort preference. Alternate vaginal anchor means may be made of various sizes, lengths, girths, etc., to suite a wide variety of user preferences.

A drainage conduit is fixed at an upper end thereof to the drainage aperture, so as to conduct urine collected in the trough therethrough and into a suitable receptacle, such as a reservoir bag, toilet, bed pan, or the like. The drainage conduit has at a lower end a valve means that has an open position and a closed position.

Preferably, the at least one side wall includes at least one attachment aperture therethrough, such that the device may be fixed to articles of clothing with straps, buttons, or the like. One of the apertures is preferably formed through the at least one side wall below the vaginal anchor means. Also in the preferred embodiment, one of the apertures is formed through the at least one side wall above the drainage conduit. The side walls may be made thicker in order to accommodate additional attachment means such as loop holes, or the like.

In use, the trough is fixed against the female so as to substantially encompass the female's labia area. The vaginal anchor means is at least partially inserted in the female's vagina, if desired. With the valve means in the closed position, the trough and the drainage conduit may collect urine from the urethra without leaking through the open top end of the trough, the material of the trough and the attachment apertures sealing the device against the female. The at least one side wall may further include a less flexible ring region for forming a seal against the female's labia area. As such, the female may use the device in either a prone or an upright position, and all the while the device is held firmly against the female to prevent urine leakage therearound. Optionally, a V-shaped clip, made of soft but resilient material, or other friction-based attachment means may be included for securing the trough to the female's clitoris, if desired. The V-shaped clip may assume an alternate shape for gripping the clitoris, such as U-shaped, or the like.

The present device is an incontinence device that is able to lie substantially flat between the woman and one or more garments, yet still maintain a suitable seal around the woman's urethra and prevent leaking when the woman is in either a prone or an upright position. The present invention is comfortable to wear, and allows the option of a removable vaginally-inserted anchoring means of various shapes, sizes, and orientations so as to allow for individual comfort preferences. The present device allows for use with a urine bag, if desired, secured around the user's leg, for example, or for direct discharge directly into a toilet, bed pan, or the like. The present invention provides a drainage conduit that is flexible and that has an easy-to-use valve means to selectively open or close the drainage conduit. The present device further provides for a variety of additional attachment means, including garments that are made to more firmly, yet comfortably, hold the device in place at attachment apertures. The present invention is further made from a comfortable, safe, flexible, either transparent or translucent material that is easily either washed or disposed of. The present device further provides additional attachment means that the user can use as necessary or as preferred. The present invention also includes a drainage tube that is adjustable, flexible so that it can be oriented either forward or rearward, and retractable and collapsible. Other features and advantages of the present invention will become apparent from the following more detailed description, taken in conjunction with the accompanying drawings, which illustrate, by way of example, the principles of the invention.

DESCRIPTION OF THE DRAWINGS

FIG. 1 is a front elevation view of an incontinence device of the invention in use;

FIG. 2 is a front elevation view of the incontinence device attached to a garment, namely a pair of panties in phantom outline;

FIG. 3 is a rear elevation view of the incontinence device as attached to a thong;

FIG. 6 is a right-side elevation view of the incontinence device showing its position in-use;

FIG. 7 is a rear elevation view of the incontinence device attached to a belt with straps. and FIG. 8 is a bottom plan view of the incontinence device attached to an alternate pair of panties, further illustrating an alternate valve means clamp and accordion folds of the drainage tube, the tube being in a retracted position.

DETAILED DESCRIPTION OF THE PREFERRED EMBODIMENT

Figure 4:
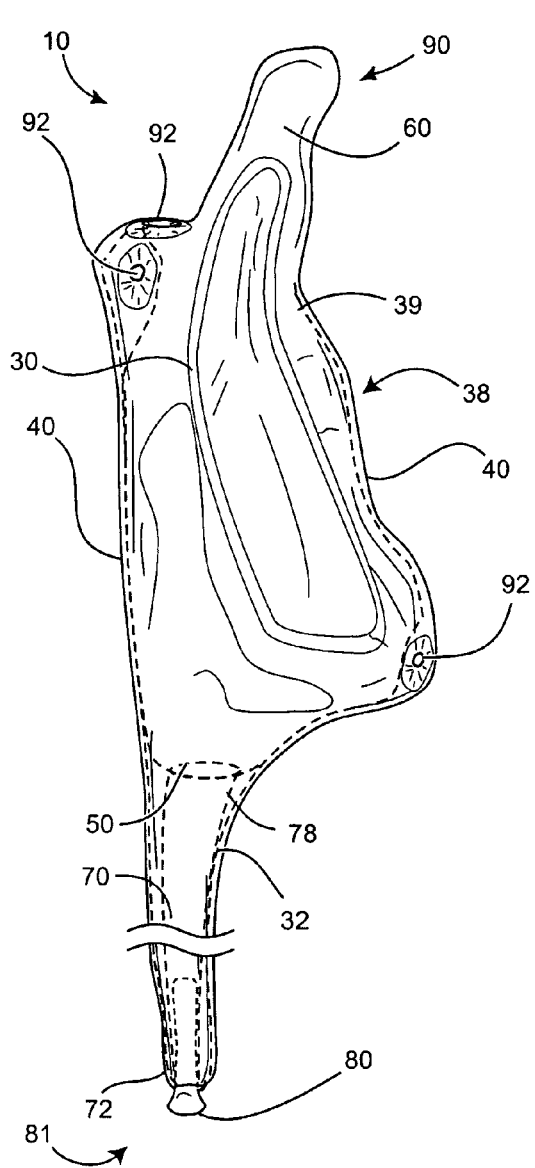
FIG. 4 is an enlarged perspective view of the incontinence device illustrating a drainage conduit having a plug as the valve means, and an elongated trough.

FIGS. 1, 2, 4, 5 and 6 illustrate an incontinence device 10 for wearing by a female 20 having a labia area 24, a urethra 25, bladder 27, pubic bone 23, a clitoris 22, and a vagina 26. A urine collection trough 30 has an elongated open top end 38 that is adapted to fit around the labia area 24 of the female 20, encompassing her urethra 25.

The trough 30 has at least one non-rigid side wall 40, preferably being made from a resilient silicone rubber, latex, vinyl, medical-grade rubber, or the like, and is made from a relatively thin opaque, transparent or translucent such resilient material so that the device will lie substantially flat against the female 20 when worn between the female 20 and an article of clothing 28. The trough 30 may be made in any color or transparency.

The trough 30 further includes a drainage aperture 50 in a lower portion 32 thereof, and a vaginal anchor means 60 at an upper portion 39 thereof. The vaginal anchor means 60 is preferably a resilient protruding member 90 fixed to the upper portion 39 of the side wall 40 of the trough 30 (FIG. 5), and preferably extends away from the trough 30 at between a 45° and a 135° angle, depending on the female's preference (FIG. 6). Preferably, but not necessarily, the protruding member 90 is removably fixed to the upper portion 39, such as by a mechanical fastening means such as mechanical snaps, tongue-in-groove, nail posts, or the like. As such, the woman 20 may decide whether or not to use the device with the vaginal anchor means 60, or may select an alternate vaginal anchor means 60 based on comfort preference. Alternate vaginal anchor means 60 may be made of various sizes, lengths, girths, or may be angle adjustable, etc., to suite a wide variety of users' preferences. Further, the trough 30 may extend up at least partially into the vaginal anchor means 60, such as illustrated in FIG. 4.

Figure 5:
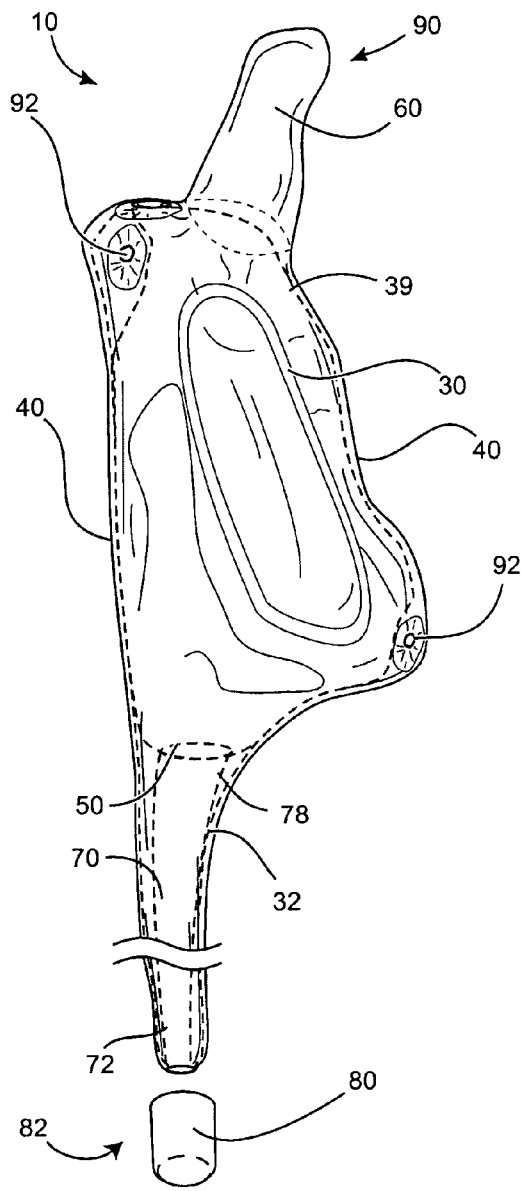
FIG. 5 is an enlarged perspective view of an alternate embodiment of the incontinence device, illustrating a drainage conduit wherein the valve means is a friction-fit cap.

Optional undergarments 28 may be used specifically for holding the device 10 in place on the female 20. Such optional undergarments 28 may be adjustable so as to fit all sizes and shapes of females 20. One of the attachment apertures 92 is preferably proximate a forward top end of the trough 30 above the drainage conduit 70, and one of the attachment apertures 92 is preferably proximate a lower rearward end of the trough 30 below the vaginal anchor means 60 (FIGS. 4 and 5).

A drainage conduit 70 is fixed at an upper end 78 thereof to the drainage aperture 50, so as to conduct urine collected in the trough 30 therethrough. The drainage conduit has at a lower end 72 a valve means 80 that has an open position 81 and a closed position 82. The valve means 80 may be a mechanical clamp 85 that, when fixed to the drainage conduit 70 occludes same. Alternately, the valve means 85 may be a cap or plug (not shown) that is adapted to fit on the lower end 72 of the drainage conduit 70 frictionally. Further, the drainage conduit 70 may include accordion folds 75 (FIG. 8) such that the drainage conduit 70 may be selectively extended, such as when emptying urine from the device 10, or retracted, such as while wearing during normal use.

Preferably, the at least one side wall 40 includes at least one attachment aperture 92 therethrough, such that the device 10 may be fixed to articles of clothing 28 (FIGS. 1-4, 6-8) with straps 29, buttons (not shown), hook-and-loop type fastening material (not shown), additional strap or holding material (not shown) incorporated into the article of clothing 28 running from the front side of the female 20 to the back side (not shown), or the like. One of the apertures 92 is preferably formed through the at least one side wall 40 below the vaginal anchor means 60 (FIG. 5). Also in the preferred embodiment, one of the apertures 92 is formed through the at least one side wall 40 above the drainage conduit 70. Optionally, the at least one attachment aperture 92 may further include a loop of material (not shown) for engaging straps or other attachment means of the articles of clothing 28.

In use, the trough 30 is fixed against the female 20 so as to substantially encompass the female's labia area 24 (FIG. 6). The vaginal anchor means 60 is at least partially inserted in the female's vagina 26. With the valve means 80 in the closed position 82, the trough 30 and the drainage conduit 70 may collect urine from the urethra 24 without leaking through the open top end 38 of the trough 30. The at least one side wall 40 may include a less flexible ring 33 region for forming a seal against the female's labia area 24. As such, the female 20 may use the device 10 in either a prone or an upright position (not shown), and all the while the device 10 is held firmly against the female to prevent urine leakage therearound. Optionally, a V-shaped clip or other friction-based or cling-based attachment means (not shown) may be included for securing the trough 30 to the female's clitoris, if desired. Such a clip includes material that clings to or is frictionally held to the area between the urethra 25 and the clitoris of the female 24, such as a thin plastic, vinyl, latex, or silicon material.

While a particular form of the invention has been illustrated and described, it will be apparent that various modifications can be made without departing from the spirit and scope of the invention. For example, various colors, opacities, and trough 30 shapes may be made. Accordingly, it is not intended that the invention be limited, except as by the appended claims.

What is claimed is:

1. An incontinence device for wearing by a female, comprising:
   a urine collection trough having an elongated open top end and at least one non-rigid side wall, a lower portion of the trough including a drainage aperture, an upper portion of the trough including a vaginal anchor means comprising a resilient protruding member ; and
   a drainage conduit fixed at an upper end to the drainage aperture for conducting urine therethrough, the drainage conduit having at a lower end a valve means having an open and a closed position;
   whereby with the trough fixed against the female and substantially encompassing the female's labia area, and with the vaginal anchor means inserted at least partially in the female's vagina, and with the valve means in the closed position, urine may be collected in the trough and drainage conduit and selectively released by actuating the valve means.

2. The incontinence device of claim 1 wherein the vaginal anchor means is a resilient protruding member fixed to the upper portion of the side wall of the trough.

3. The incontinence device of claim 1 wherein the vaginal anchor means is selectively removable.

4. The incontinence device of claim 1 wherein the valve means is a mechanical clamp.

5. The incontinence device of claim 1 wherein the valve means is a mechanical cap adapted to fit frictionally onto the lower end of the drainage conduit.

6. The incontinence device of claim 1 wherein the valve means is a mechanical plug adapted to fit frictionally into the lower end of the drainage conduit.

7. The incontinence device of claim 1 wherein the at least one side wall of the trough further includes at least one attachment aperture therethrough, whereby articles of clothing may be fastened thereto to hold the incontinence device in place against the female.

8. The incontinence device of claim 7 wherein the at least one side wall of the trough further includes two of the attachment apertures therethrough, one of the attachment apertures proximate a forward top end of the trough and one of the attachment apertures proximate a lower rearward end of the trough.

9. The incontinence device of claim 1 wherein the drainage conduit includes accordion folds along the length thereof, whereby the drainage conduit is selectively extendable and retractable.

10. The incontinence device of claim 1 wherein the trough is formed from a cling vinyl material.

11. The incontinence device of claim 1 wherein the trough is formed from a silicone rubber material.

12. The incontinence device of claim 1 wherein the trough is formed from a latex material.

13. The incontinence device of claim 1 wherein the trough is formed from a medical grade rubber material.

\* \* \* \* \*